United States Patent

Davis et al.

[11] 4,175,134
[45] Nov. 20, 1979

[54] PHENOXYBENZYL ESTER PESTICIDES

[75] Inventors: Royston H. Davis; Robert J. G. Searle, both of Sittingbourne, England

[73] Assignee: Shell Oil Company, Houston, Tex.

[21] Appl. No.: 898,367

[22] Filed: Apr. 17, 1978

Related U.S. Application Data

[62] Division of Ser. No. 791,813, Apr. 28, 1977.

[30] Foreign Application Priority Data

Jun. 17, 1976 [GB] United Kingdom ............. 25144/76

[51] Int. Cl.$^2$ ................. A01N 9/12; C07C 153/11
[52] U.S. Cl. ........................... 424/301; 260/455 R; 560/124
[58] Field of Search ................. 560/124; 260/455 R; 424/301

[56] References Cited

U.S. PATENT DOCUMENTS 3,761,506  9/1973  Osbond et al. .................. 560/124

OTHER PUBLICATIONS

Matsuo, et al., Agr. Biol. Chem., 40/D, pp. 247-249 (1976).

Primary Examiner—John M. Ford
Assistant Examiner—Robert C. Whittenbaugh

[57] ABSTRACT

Certain esters of alpha-substituted-phenoxybenzyl alcohols of the formula

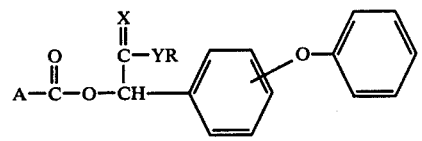

wherein A represents certain optionally substituted aralkyl, alkyl or cyclopropyl groups at least one of X and Y is sulfur and the other independently represents oxygen or sulfur and R represents certain alkyl, alkenyl, alkynyl, aralkyl, alkaryl or aryl groups, hydrogen or a salt-forming cation, are useful as pesticides.

8 Claims, No Drawings

PHENOXYBENZYL ESTER PESTICIDES

This is a division, of application Ser. No. 791,813, filed Apr. 28, 1977.

FIELD OF THE INVENTION

The present invention relates to new esters of alpha-substituted-phenoxybenzyl alcohols, their preparation, their use as pesticides and to pesticidal compositions containing the new esters.

BACKGROUND OF THE INVENTION

Synthetic pyrethrin-like compounds have been produced over the years in attempts to duplicate or improve upon the activity spectrum of natural pyrethrins. The compounds of the present invention are derived from esters known to exhibit pyrethrin-like activity but are uniquely characterized by an alpha-carboxylate substituent in the alcohol portion of the molecule. These new compounds possess the desirable low order of toxicity to warm-blooded animals while having useful insecticidal, acaricidal and tickicidal properties such that they are very suitable for a variety of applications, e.g., on crops, and for domestic needs.

SUMMARY OF THE INVENTION

The present invention is directed to certain alpha-carboxylated-phenoxybenzyl esters having the formula I

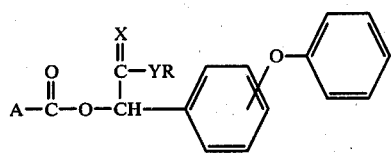

and their salts, wherein A represents an optionally substituted benzyl group, an optionally substituted alkyl or cyclopropyl group; X and Y each independently represent oxygen or sulfur and R represents an alkyl, alkenyl or alkynyl group each containing up to 6 carbon atoms, an aralkyl, alkaryl or aryl group each containing up to 10 carbon atoms, a hydrogen atom or a salt-forming cation selected from an alkali metal, an alkaline earth metal, ammonia or a hydrocarbyl-ammonium compound, e.g., tetraalkyl ammonium in which each alkyl group contains from 1 to 10 carbon atoms.

It should be noted that optical isomers, cis-trans isomers and other kinds of geometric isomers of the compounds according to formula I are within the scope of the present invention as well as racemates and mixtures of isomers of one or more of the compounds according to formula I.

The above described alpha-carboxylated phenoxybenzyl esters are useful as pesticides and particularly as insecticides, acaricides and tickicides.

Suitable compounds contemplated within the scope of the invention include:
alpha-propenyloxycarbonyl-4-phenoxybenzyl 2,2-dibromovinyl-3,3-dimethylcyclopropane carboxylate;
alpha-ammoniumthiocarbonyl-3-phenoxybenzyl 2,2,3,3-tetramethylcyclopropane carboxylate;
alpha-(tetramethylammonium)oxycarbonyl-3-phenoxybenzyl 2,2-dichlorovinyl-3,3-dimethylcyclopropane carboxylate;
alpha-ethynyloxycarbonyl-2-phenoxybenzyl 2,2-dimethylvinyl-3,3-dimethylcyclopropane carboxylate;
alpha-phenylthiocarbonyl-3-phenoxybenzyl alpha'-isopropyl-2-chlorobenzylcarboxylate;
alpha-benzylthiocarbonyl-4-phenoxybenzyl alpha'-ethyl-2-ethoxybenzylcarboxylate;
alpha-tolyloxycarbonyl-3-phenoxybenzyl 2,2,3,3-tetramethylcyclopropane carboxylate; and
alpha-ethyloxycarbonyl-4-phenoxybenzyl alpha'-isopropyl-4-bromobenzylcarboxylate;

When A represents an optionally substituted benzyl group in formula I, preferred compounds are those containing a substituted benzyl group of formula

wherein Z represents a halogen atom having an atomic number from 9 to 35, inclusive, preferably a chlorine atom, or an alkoxy group containing from 1 to 4 carbon atoms, e.g., methoxy, and Q represents an alkyl group containing from 1 to 6 carbon atoms, especially a branched chain group such as an isopropyl group.

When A represents an optionally substituted alkyl group in formula I, preferred compounds are those in which the lower alkyl group has the formula

wherein W represents an alkyl group containing from 1 to 6 carbon atoms or an alkenyl group containing from 2 to 6 carbon atoms. The substituent W may be branched, such as an isopropyl, isobutyl or isoamyl group or may be straight chain, such as methyl, ethyl, n-propyl, n-butyl or n-hexyl. When W is an alkenyl group it may suitably be allyl, butenyl or pentyl. Preferably, W is branched chain such as isopropyl.

When A represents a cyclopropyl group in formula I, the preferred compounds are those containing a cyclopropyl group of formula

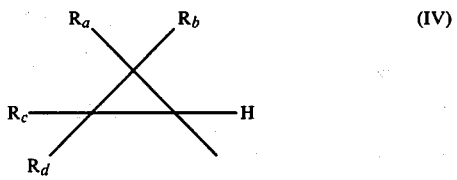

wherein $R_a$ and $R_b$ each represent an alkyl group containing from 1 to 6 carbon atoms, especially methyl, or a halogen atom having an atomic number from 9 to 35, inclusive, especially a chlorine atom; or $R_a$ and $R_b$ together represent an alkylene group containing from 2 to 6, especially 3 carbon atoms; or $R_a$ represents a hydrogen atom and $R_b$ represents an alkenyl group containing from 2 to 6 carbon atoms, especially an isobutenyl group, or an haloalkenyl group containing from 2 to 6 carbon atoms and from 1 to 3 chlorine or bromine atoms, especially a mono- or dichlorovinyl group; $R_c$ and $R_d$ each represent an alkyl group containing from 1 to 6 carbon atoms, especially methyl, or $R_c$ is a hydrogen atom and $R_d$ is an alkenyl group containing from 2 to 6 carbon atoms, especially an isobutenyl group, or an haloalkenyl group containing from 2 to 6 carbon atoms and from 1 to 3 chlorine or bromine atoms, especially a mono- or dichlorovinyl group; or $R_c$ and $R_d$ together represent an alkylene group containing from 2 to 6, especially 3 carbon atoms.

Examples of some particularly preferred compounds according to the present invention are:

alpha-methyloxycarbonyl-3-phenoxybenzyl 2,2,3,3-tetramethyl cyclopropane carboxylate;

alpha-methylthiocarbonyl-3-phenoxybenzyl 2,2,3,3-tetramethyl cyclopropane carboxylate;

alpha-methyloxycarbonyl-3-phenoxybenzyl 2,2-dichlorovinyl-3,3-dimethylcyclopropane carboxylate;

alpha-methylthiocarbonyl-3-phenoxybenzyl 2,2-dimethylvinyl-3,3-dimethylcyclopropane carboxylate;

alpha-methoxycarbonyl 3-phenoxybenzyl alpha'-isopropyl-4-chlorobenzylcarboxylate; and alpha-2-butylthiocarbonyl-3-phenoxybenzyl 2,2,3,3-tetramethylcyclopropane carboxylate.

The process for the preparation of the novel compounds of the invention may be carried out by known methods. Thus the novel compounds of formula I wherein Y is a sulphur atom and X is an oxygen atom may be prepared by a process which comprises reacting the corresponding alpha-cyanobenzyl ester of formula:

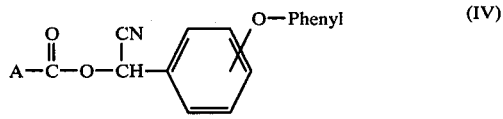

(IV)

wherein A has the meaning defined for formula I, with a thiol of formula R'—SH in the presence of excess anhydrous hydrogen halide, preferably hydrogen chloride and subsequently treating the product formed with a hydrolysing agent. A suitable hydrolysing agent may be water or a dilute aqueous solution of an alkali such as potassium carbonate. The reaction is suitably carried out in an inert solvent, for example an ether such as diethyl ether or dioxan and may be effected at temperatures below about 5° C., preferably 0° C.

Those compounds of the invention wherein both X and Y represent oxygen atoms may also be prepared from the corresponding alpha-cyanobenzyl ester of formula IV by a process which comprises reacting the said ester with an alcohol of formula $R^1$—OH in the presence of excess anhydrous hydrogen halide, preferably the chloride and subsequently treating the product formed with a hydrolysing agent.

Alternatively, the compounds of the invention wherein X is a sulphur atom and Y is an oxygen atom may be prepared by a process which comprises reacting a corresponding alpha-thioamidobenzyl ester of formula:

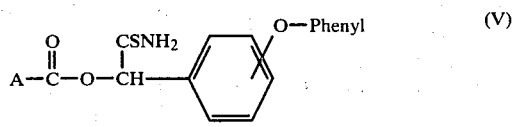

(V)

wherein A has the meaning defined in formula I, with a halide of formula $R^1$-halide, preferably an iodide, in the presence of acetonitrile. The reaction may be effected at room temperature over a period of 4 to 6 days. The reaction mixture may be worked up in any conventional way.

The alpha-carboxylated-phenoxybenzyl esters of the invention and salts thereof are of interest as pesticides, in particular as insecticides, tickicides and acaricides for agricultural and domestic outlets. The invention therefore includes within its scope pesticidal compositions comprising a carrier and/or a surface-active agent together with, as active ingredient, an alpha-carboxylated-phenoxybenzyl ester of formula I. The invention also includes a method of combating insect, tick and/or acarid pests at a locus which comprises applying to the locus a pesticidally effective amount of an alpha-carboxylated-phenoxybenzyl ester of the invention or salt thereof or composition containing such a compound.

The term 'carrier' as used herein means a material, which may be inorganic or organic and of synthetic or natural origin, with which the active compound is mixed or formulated to facilitate its application to the plant, seed, soil or other object to be treated, or its storage, transport or handling. The carrier may be a solid or a liquid. Any of the materials usually applied in formulating pesticides, herbicides, or fungicides may be used as the carrier.

Suitable solid carriers are natural and synthetic clays and silicates, for example natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonates; calcium sulphate; synthetic hydrated silicon oxides and synthetic calcium or aluminum silicates; elements for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilizers, for example superphosphates.

Suitable liquid carriers are water, alcohols, for example, isopropanol and glycols; ketones for example, acetone, methyl ethyl ketone, and cyclohexanone; ethers; aromatic hydrocarbons, for example, benzene, toluene and xylene; petroleum fractions, for example, kerosine and light mineral oils; chlorinated hydrocarbons, for example, carbon tetrachloride, perchloroethylene, trichloroethane; and liquefied normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating pesticides herbicides or fungicides, may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products; alkali or alkaline earth metal salts, preferably sodium salts, or sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 and 75% of toxicant and usually contain, in addition, to solid carrier, 3 1–0% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676–0.152 mm), and may be manufactured by agglomeration or impregnation techniques. Generally, granules will contain ½–25% w toxicant and 0–10% w of additives such as stabilizers, slow release modifiers and binding agents. Emulsifiable concentrates usually contain, in addition to the solvent and, when necessary, co-solvent, 10–50% w toxicant, 2–20% w/v emulsifiers and 0–20% w/v of appropriate additives such as stabilizers, penetrants and corrosion inhibitors. Suspension concentrates are compounded so as to obtain a stable, non-sedimenting flowable product and usually contain 10–75% w toxicant, 0.5–15% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing pesticidal, herbicidal or fungicidal properties.

EXAMPLES

The invention is further illustrated by the following examples which are for the purpose of illustration only and should not be regarded as limiting the invention in any way.

EXAMPLE 1
alpha-isopropylthiocarbonyl-3-phenoxybenzyl 2,2,3,3-tetramethyl cyclopropanecarboxylate Dry hydrogen chloride gas was bubbled through a solution of isopropylthiol (10 ml) and 3-phenoxy-alpha-cyanobenzyl 2,2,3,3-tetramethylcyclopropanecarboxylate (3 g) in ether (100 ml) at 0° for 4 hours. The cold solution was then added with care to a stirred 40% potassium carbonate solution (100 ml) and the mixture stirred vigorously for 4 hours at 30° C. The ethereal layer was separated, dried over magnesium sulphate and the solvent removed under reduced pressure. The residue was purified by column chromatography on silica gel using a 1:7 mixture of ether in hexane as eluent. The required product was obtained as an oil $n_D^{19.5}$ 1.5490.

Analysis: Calculated for $C_{25}H_{30}O_4S$: C 70.4; H 7.1%: Found: C 70.8; H 7.2%.

EXAMPLE 2
alpha-Methylthiocarbonyl-3-phenoxybenzyl 2,2-dichlorovinyl-3,3-dimethylcyclopropanecarboxylate Alpha-thioamido-3-phenoxybenzyl 2,2-dichlorovinyl-3,3-dimethylcyclopropanecarboxylate (4 g) and methyl iodide (8 g) was dissolved in acetonitrile (30 ml) and the solution left to stand under atmospheric conditions for 5 days. The solution was decanted from the ammonium iodide crystals which precipitated and the solvent removed under reduced pressure. The residue was purified by chromatography on silica gel using a 1:1 mixture of dichloromethane in hexane as eluent. The required product was obtained as an oil $n_D^{20}$ 1.5777.

Analysis: Calculated for $C_{23}H_{22}O_4SCl_2$: C 59.4; H 4.8; Cl 15.2%: Found: C 59.7; H 4.8; Cl 14.8%.

EXAMPLE 3
Alpha-methylthiocarbonyl-3-phenoxybenzyl alpha'-isopropyl-4-methoxy benzylcarboxylate A solution of alpha-cyano-3-phenoxybenzyl alpha'-isopropyl-4-methoxybenzylcarboxylate (2.0 g) and methylthiol (20 ml) in ether (150 ml) was cooled to −5° C. and dry hydrogen chloride bubbled through the solution for 4 hours. Water (100 ml) was added carefully to the reaction mixture and the ethereal layer was separated and dried over magnesium sulphate. The solvent was removed to give a pale yellow oil which was purified by chromatography on silica gel using a 4:1 mixture of hexane:ether. The required product was obtained as an oil, $n_D^{19.5}$ 1.5708.

Analysis: Calculated for $C_{27}H_{28}O_5S$: C 69.8; H 6.1%: Found: C 69.0; H 6.4%.

EXAMPLES 4–11

Following procedures similar to those described in the foregoing Examples, further compounds were prepared and are described in Table I.

TABLE I

| Example Number | Compound | R.I. or m.p. | analysis | |
|---|---|---|---|---|
| 4 | alpha-methoxycarbonyl-3-phenoxybenzyl 2,2,3,3-tetramethylcyclopropane carboxylate. | 48–49° C. | Calculated for $C_{23}H_{26}O_5$ Found: | C 72.3 ; H 6.9% C 72.6 ; H 6.9% |
| 5 | alpha-methylthiocarbonyl-3-phenoxybenzyl 2,2,3,3-tetramethylcycloproprane carboxylate | $n_D^{19}$ 1.5505 | Calculated for $C_{23}H_{26}SO_4$ Found: | C 69.3 ; H 6.6% C 69.5 ; H 6.6% |

TABLE I-continued

| Example Number | Compound | R.I. or m.p. | analysis | |
|---|---|---|---|---|
| 6 | alpha-methoxycarbonyl-3-phenoxybenzyl alpha'-isopropyl-4-chlorobenzylcarboxylate | $n_D^{19}$ 1.5639 | Calculated for $C_{26}H_{25}ClO_5$: | C 68.9 ; H 5.6% |
| | | | Found: | C 68.9 ; H 5.6% |
| 7 | alpha-methoxycarbonyl-3-phenoxybenzyl 2,2-dichlorovinyl-3,3-dimethylcyclopropane carboxylate | $n_D^{19}$ 1.5610 | Calculated for $C_{23}H_{22}Cl_2O_5$: | C 61.5 ; H 4.9% |
| | | | Found: | C 61.7 ; H 5.0% |
| 8 | alpha-methylthiocarbonyl-3-phenoxybenzyl alpha'-isopropyl-4-chlorobenzylcarboxylate | $n_D^{20.5}$ 1.5829 | Calculated for $C_{26}H_{25}Cl\,SO_4$: | C 66.6 ; H 5.4 ; Cl 7.6% |
| | | | Found: | C 66.6 ; H 5.3; Cl 7.2% |
| 9 | alpha-methylthiocarbonyl-3-phenoxybenzyl 2,2-dimethyl-3-isobutenylcyclopropane carboxylate | $n_D^{18.5}$ 1.5622 | Calculated for $C_{25}H_{28}SO_4$: | C 70.7 ; H 6.7% |
| | | | Found: | C 71.5 ; H 6.9% |
| 10 | alpha-but-2-ylthiocarbonyl-3-phenoxybenzyl 2,2,3,3-tetramethylcyclopropanecarboxylate | $n_D^{18.5}$ 1.5484 | Calculated for $C_{26}H_{32}SO_4$ | C 70.9 ; H 7.3% |
| | | | Found: | C 71.2 ; H 7.4% |
| 11 | alpha-methylthiocarbonyl-3-phenoxybenzyl 2-methylheptan-3-ylcarboxylate | $n_D^{20}$ 1.5295 | Calculated for $C_{24}H_{30}SO_4$: | C 69.5 ; H 7.3% |
| | | | Found: | C 69.7 ; H 7.3% |

EXAMPLE 12

The insecticidal and tickicidal activity of the compounds according to the present invention was assessed employing the following pests:

Insects:
  *Musca domestica* (M.d.)
  *Phaedon cochleariae* (P.c.)
  *Megoura viciae* (M.v.)
  *Spodoptera littoralis* (S.l.)
  *Heliothis zea* (H.z.)

Ticks:
  *Boophilus microphus* (B.m.)

The test methods employed for each species appear below:

(i) *Musca domestica* (M.d.). A 0.4% by weight solution in acetone of the compound to be tested was prepared and taken up in a micrometer syringe. Two to three day old adult female houseflies (*Musca domestica*) were anaesthetized with carbon dioxide, and 1 µl of the test solution was applied to the ventral side of the abdomen of each fly, 20 flies being tested. The treated files were held in glass jars covered with paper tissue held by an elastic band. Cotton-wool pads soaked in dilute sugar solution were placed on top of the tissue a food. After 24 hours the percentage of dead and moribund flies were recorded. (ii) *Phaedon cochleariae* (P.c.) and *Megoura viciae* (M.v.). The compounds were formulated as solutions or suspensions in water containing 20% by weight of acetone and 0.05% by weight of Triton X-100 as wetting agent. The formulations contained 0.4% by weight of the compound to be tested. Turnip and broad bean plants, trimmed to one leaf each, were sprayed on the undersurface of the leaf with the above formulation. Spraying was effected with a spraying machine, delivering 340 liters per hectare, the plants passing under the spray on a moving belt. After spraying, the plants were left for ½–1 hour drying period and then each plant was enclosed within a 450 ml bottle from which the bottom had been removed. Ten adult 2-3 week old mustard beetles (*Phaedon cochleariae*) were placed on the sprayed leaf of each turnip plant and ten apterous (6 day old) vetch aphids (*Megoura viciae*) were placed on the sprayed leaf of each broad bean plant. The open ends of the bottle were then closed with squares of paper tissue held with elastic bands. Mortality counts were made after 24 hours.

(iii) *Spodoptera littoralis* (S.l.) Pairs of leaves were removed from broad bean plants and placed on filter paper inside plastic petri dishes. The leaves were sprayed as in (ii), using the same concentrations. After spraying the leaves were left for ½–1 hour drying period and then each leaf pair was infested with ten larvae of the Egyptian cotton leafworm (*Spodoptera littoralis*). After 24 hours the percentage of dead and moribund larvae were recorded.

(iv) *Boophilus microplus* (B.m.). The compounds to be tested were formulated as solutions or fine suspensions in acetone containing 10% by weight of polyethylene glycol having an average molecular weight of 400. The formulations contained 0.1% by weight of the compound to be tested. 1 ml of the above-mentioned solution was applied evenly to a filter paper situated inside a petri dish. After the paper was sufficiently dry it was folded in half and partly crimped along the outer edge to form a packet. About 80–100 larval ticks (*Boophilus microplus*) were transferred into the packet which was then sealed completely. The packets were placed inside an incubator, maintained at 27° C. and 80% relative humidity, before assessing mortality 24 hours later.

(v) *Heliothis zea* (H.z.). A 0.2% by weight solution of the compound to be tested was prepared by adding 2 ml of a 1% acetone solution to 8 ml of 0.05% AHOX 1045A solution. The cut broad bean plant was sprayed with 4 ml of test solution using a hand sprayer. Immediately after spraying 5 larvae of the corn earworm (*Heliothis zea*) were transferred to each plant which was inserted into water through the center hole of a test board and covered with a wire screen. 44–46 hours after spraying the percentage of dead and moribund larvae were recorded.

The results of those tests are shown in Table II in which the test species are identified by the initials noted above and A denotes complete kill, B some kill and C no kill of the test species.

EXAMPLE 13

The acaricidal activity of the compounds according to the invention was assessed employing the following pest:

*Tetranychus urticae* (T.u.)

The test method employed was as follows. Leaf discs cut from french bean plants were inoculated with 10 red spider mites in the manner described in Example 12 for the insects *Phaedon cochleariae* and *Megoura viciae* 1 hour after drying. Mortality counts were made 24 hours after inoculation. The results of these tests are shown in Table III employing the same notation as used in the previous example.

TABLE II

| Compound Example No. | M.d. | P.c. | S.l. | M.v. | B.m. | H.z. |
| --- | --- | --- | --- | --- | --- | --- |
| 1 | | | | | | A |
| 2 | A | B | A | A | A | A |
| 4 | B | A | B | B | A | A |
| 5 | A | B | A | A | A | A |
| 6 | B | A | A | A | A | A |
| 7 | A | A | A | A | A | A |
| 8 | A | C | A | A | A | A |
| 9 | A | B | B | A | A | A |
| 10 | C | C | B | A | A | A |
| 11 | | | | | | A |

TABLE III

| Acaricidal Activity | |
| --- | --- |
| Compound of Example No. | T.U. |
| 5 | B |
| 8 | B |

We claim:

1. An alpha-carboxylated-phenoxybenzyl ester having the formula

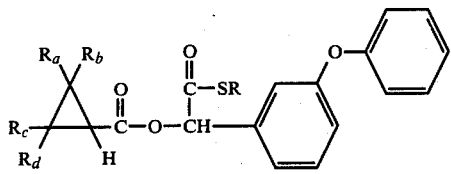

wherein $R_a$ and $R_b$ each represent an alkyl group containing from 1 to 6 carbon atoms, or a halogen atom having an atomic number from 9 to 35, inclusive; $R_c$ and $R_d$ each represent an alkyl group containing from 1 to 6 carbon atoms, or $R_c$ is a hydrogen atom and $R_d$ is an alkenyl group containing from 2 to 6 carbon atoms or a haloalkenyl group containing from 2 to 6 carbon atoms and from 1 to 3 chlorine or bromine atoms; and R represents an alkyl, alkenyl or alkynyl group each containing up to 6 carbon atoms, an aralkyl, alkaryl or aryl group each containing up to 10 carbon atoms, a hydrogen atom or a salt-forming cation selected from an alkali metal, an alkaline earth metal, ammonia or a tetraalkylammonium compound in which each alkyl group contains from 1 to 10 carbon atoms.

2. An alpha-carboxylated-phenoxybenzyl ester according to claim 1 wherein $R_a$ and $R_b$ each represent methyl; $R_c$ represents a hydrogen atom and $R_d$ represent dichlorovinyl.

3. An alpha-carboxylated-phenoxybenzyl ester according to claim 1 wherein $R_a$, $R_b$, $R_c$ and $R_d$ each represent methyl.

4. An alpha-carboxylated-phenoxybenzyl ester according to claim 1 wherein $R_a$ and $R_b$ each represent methyl; $R_c$ represents a hydrogen atom, and $R_d$ represents isobutenyl.

5. A method of combating tick, insect and/or acarid pests at a locus which comprises applying to the locus a tickicidal, insecticidal and/or acaricidally effective amount of an alpha-carboxylated-phenoxybenzyl ester as claimed in claim 1 or a composition thereof.

6. A method according to claim 5 wherein the ester is selected from alpha-isopropylthiocarbonyl-3-phenoxybenzyl 2,2,3,3-tetramethylcyclopropane carboxylate, alpha-methylthiocarbonyl-3-phenoxybenzyl 2,2,3,3-tetramethylcyclopropane carboxylate, alpha-methylthiocarbonyl-3-phenoxybenzyl 2,2-dichlorovinyl-3,3-dimethylcyclopropane carboxylate, and alpha-but-2-ylthiocarbonyl-3-phenoxybenzyl 2,2,3,3-tetramethylcyclopropane carboxylate.

7. A pesticidal composition comprising a pesticidally effective amount of an alpha-carboxylated-phenoxybenzyl ester as claimed in claim 1 and at least one carrier or surface-active agent.

8. A pesticidal composition according to claim 7 wherein the alpha-carboxylated-phenoxybenzyl ester is selected from alpha-isopropylthiocarbonyl-3-phenoxybenzyl 2,2,3,3-tetramethylcyclopropane carboxylate, alpha-methylthiocarbonyl-3-phenoxybenzyl 2,2,3,3-tetramethylcyclopropane carboxylate, alpha-methylthiocarbonyl-3-phenoxybenzyl 2,2-dichlorovinyl-3,3-dimethylcyclopropane carboxylate, and alpha-but-2-ylthiocarbonyl-3-phenoxybenzyl 2,2,3,3-tetramethylcyclopropane carboxylate.

* * * * *